United States Patent [19]

Chapman et al.

[11] Patent Number: 5,632,277
[45] Date of Patent: May 27, 1997

[54] ULTRASOUND IMAGING SYSTEM EMPLOYING PHASE INVERSION SUBTRACTION TO ENHANCE THE IMAGE

[75] Inventors: Christopher S. Chapman, Redmond; John C. Lazenby, Fall City, both of Wash.

[73] Assignee: Siemens Medical Systems, Inc., Iselin, N.J.

[21] Appl. No.: 672,823

[22] Filed: Jun. 28, 1996

[51] Int. Cl.$^6$ .................................................. A61B 8/00
[52] U.S. Cl. ............................................... 128/660.07
[58] Field of Search ....................... 128/660.01, 660.02, 128/660.05, 660.07, 660.08, 661.07

[56] References Cited

U.S. PATENT DOCUMENTS

| | | | |
|---|---|---|---|
| 5,086,775 | 2/1992 | Parker et al. | 128/660.02 |
| 5,482,044 | 1/1996 | Sheng-Tzlin et al. | 128/660.07 |

*Primary Examiner*—George Manuel

[57] ABSTRACT

A method for generating an ultrasound image that enhances regions occupied by non linear scattering media. The method utilizes first and second ultrasound pulses that are alternatively transmitted into the specimen being imaged. The first and second ultrasound pulses are amplitude modulated harmonic signals, the first ultrasound pulse differing from the second ultrasound pulse by the phase of the harmonic signal. The echo signals generated by these pulses are measured and combined. In one embodiment of the present invention, the first and second ultrasound signals differ by 180 degrees and the echo signals are combined by adding the echo signals generated by each of the ultrasound pulses.

2 Claims, 1 Drawing Sheet

ULTRASOUND IMAGING SYSTEM EMPLOYING PHASE INVERSION SUBTRACTION TO ENHANCE THE IMAGE

FIELD OF THE INVENTION

The present invention relates to ultrasound imaging, and more particularly, to a method and apparatus for enhancing ultrasound images.

BACKGROUND OF THE INVENTION

Ultrasound imaging is an attractive modality for numerous diagnostic procedures because of its non-invasive nature, relatively low cost, and lack of radiation exposure. Medical ultrasound images are typically produced by generating an ultrasonic sound wave traveling in a known direction and observing the echoes created when the sound wave is scattered or bounces off of the boundaries between regions of differing density in the body. For any given direction of the ultrasound beam, the image pixels are generated by plotting a dot whose brightness is proportional to the echo's amplitude at a coordinate whose location is a function of the time after a short ultrasound pulse is send in the direction of the scan line being measured.

While ultrasound has a number of advantages over other measurement modalities, it suffers from noise problems that make the measurements difficult to interpret without some form of noise reduction. This noise results from noise in the receiver and from the individual sound scattering centers in the tissues between the transducer and some structure of interest. While various forms of averaging may be used to reduce the effects introduced by these scattering centers, averaging can do little to distinguish tissues having very similar densities. In addition, many tissues have very similar densities. Hence, generating an image of the boundary between two types of tissues is difficult if the tissues are not separated by a region having a significantly different density.

Broadly, it is the object of the present invention to provide an improved ultrasound imaging system.

It is a further object of the present invention to provide an ultrasound imaging system that can distinguish tissues based on properties other than density.

These and other objects of the present invention will become apparent to those skilled in the art from the following detailed description of the invention and the accompanying drawings.

SUMMARY OF THE INVENTION

The present invention is a method for generating an ultrasound image that enhances regions occupied by non linear scattering media. The method utilizes first and second ultrasound pulses that are alternatively transmitted into the specimen being imaged. The first and second ultrasound pulses are amplitude modulated harmonic signals. The first ultrasound pulse differs from the second ultrasound pulse by the phase of the harmonic signal. The echo signals generated by these pulses are measured and combined. In one embodiment of the present invention, the first and second ultrasound signals differ by 180 degrees in phase and the echo signals are combined by adding the echo signals generated by each of the ultrasound pulses.

DETAILED DESCRIPTION OF THE INVENTION

Figure 1:
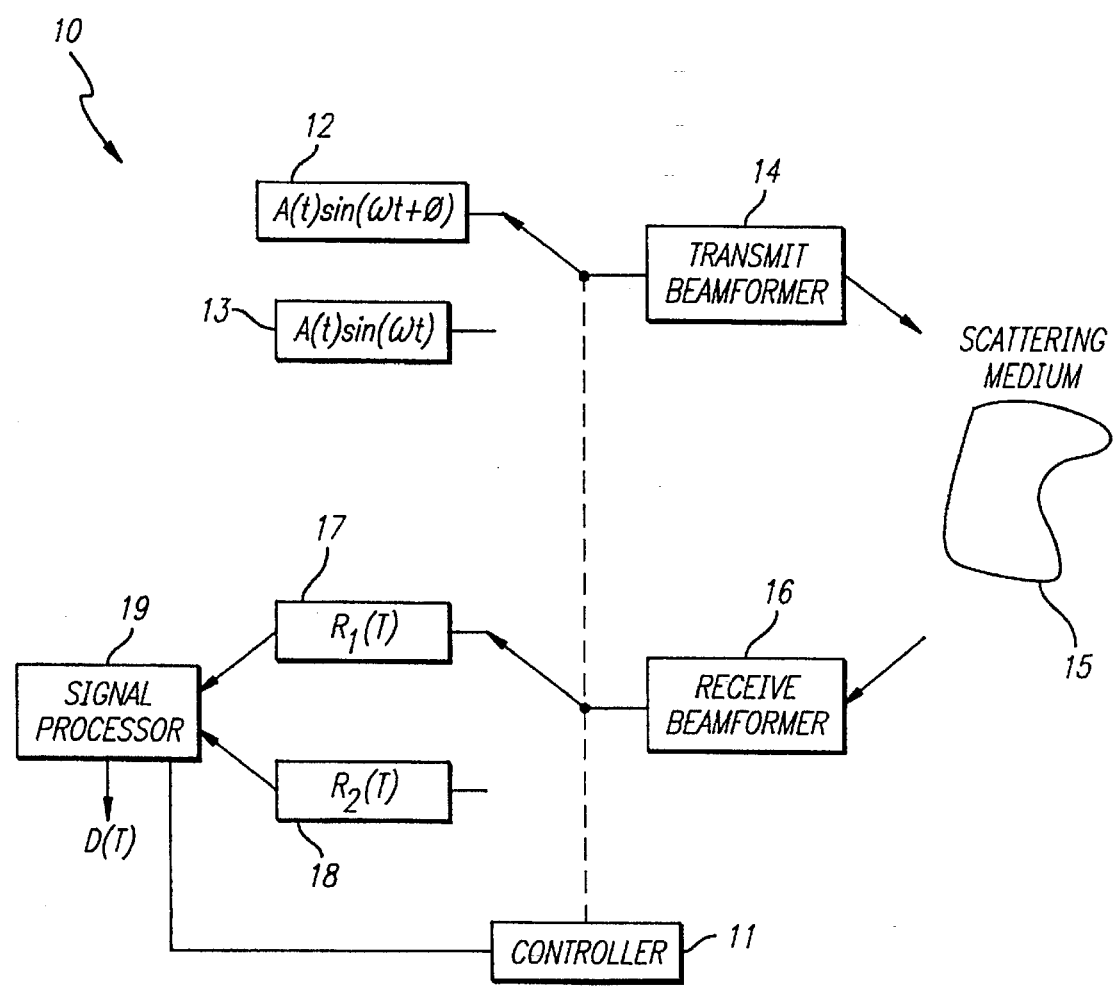
FIG. 1 is a block diagram of an ultrasound imaging system according to the present invention

In general, the ultrasound beam is generated by using an array of transducers to form a transmit beam in a given direction with respect to the array. The ultrasound pulse is an amplitude modulated pulse at a predetermined frequency, $\omega$, having an amplitude specified by an envelope function A(t). The echoes generated by this pulse are detected by the same, or a different, array of transducers that are used to form a receive beam corresponding to the transmit beam. The directional sensitivity of the microphone reduces echoes generated by multiple reflections of the sound pulse. A filter centered at frequency $\omega$ is used to reduce noise.

The present invention is based on the observation that some types of acoustic media such as flowing liquids scatter sound in a non-linear manner. With linear scattering, the returned signal is a time-shifted, amplitude-scaled version of the incident signal. Non-linear scattering produces return signals that cannot be generated by simple scaling, time-shifting, and summing of the incident signal. The phase of a sound wave reflected from the boundary of a non-linear medium is altered in a manner that depends on the phase of the incident sound pulse. Consider two sound pulse that differ in phase by 180 degrees. If these sound waves are reflected from the boundary between two linear scattering media, the resulting echoes will also differ in phase by 180 degrees. If, however, one of the media is non-linear, the phase difference will no longer be 180 degrees.

This observation may be used to construct a contrast enhancement system which emphasizes non-linear regions. For example, in one embodiment of the present invention, an image is generated by adding two successive echo sequences in which the first echo is generated by a sound pulse that differs in phase by 180 degrees with respect to the second sound pulse. Echoes generated by reflections between linear media will cancel in this arrangement, since each echo in the first sequence will be added to an echo having the same amplitude but a 180 degree phase difference in the second sequence. If, however, an echo results from a scattering center in a non-linear medium, the phases will no longer differ by 180 degrees, and hence, the two echoes will not cancel in the sum signal.

Refer now to FIG. 1 which is a block diagram of an ultrasound imaging system 10 according to the present invention. Imaging system 10 includes a signal generator that generates a first pulse 12 and a second pulse 13 that differ in phase by $\phi$ degrees. Controller 11 alternately selects these pulses for input to transmit beamformer 14 which generates the ultrasound signal that is applied to specimen 15 in direction. The echoes generated by specimen 15 in the reverse direction are detected by receive beamformer 16. The amplitude of the received echo signal as a function of time, R(t), is one of two buffers, 17 and 18, depending on the pulse used to generate the echo. A signal processor 19 then combines the echoes to form the enhanced echo signal D(t) which is treated and displayed in the same manner as a conventional ultrasound echo signal from the direction in question. The process is repeated for each beam direction to provide a two-dimensional image.

Various modifications to the present invention will become apparent to those skilled in the art from the foregoing description and accompanying drawings. Accordingly, the present invention is to be limited solely by the scope of the following claims.

What is claimed is:

1. In a method for generating an ultrasound image in which ultrasound pulses comprising amplitude modulated harmonic signals are transmitted into a specimen and echos generated by said ultrasound pulses are received, the improvement comprising: transmitting first and second ultrasound pulses into a specimen, said first and second ultrasound pulses, said first ultrasound pulse differing from said second ultrasound pulse by the phase of said harmonic signal; receiving an echo signal, $R_1(t)$, generated by said first ultrasound pulse, said echo signal being determined by the amplitude of an echo received at a transducer as a function of the time, t, after said first ultrasound pulse was transmitted; receiving an echo signal, $R_2(t)$, generated by said second ultrasound pulse, said echo signal being determined by the amplitude of an echo received at said transducer as a function of the time, t, after said second ultrasound pulse was transmitted; and combining $R_1(t)$ and $R_2(t)$ to generate an image signal $D(t)$.

2. The method of claim 1 wherein said phase difference is 180 degrees and wherein said step of combining comprising adding $R_1(t)$ to $R_2(t)$ for each t value.

* * * * *

UNITED STATES PATENT AND TRADEMARK OFFICE
CERTIFICATE OF CORRECTION

PATENT NO. : 5,632,277
DATED : May 27, 1997
INVENTOR(S) : Christopher S. Chapman and John C. Lazenby It is certified that error appears in the above-identified patent and that said Letters Patent is hereby corrected as shown below:

In claim 1, column 3, lines 4 and 5, cancel the phrase "said first and second ultrasound pulses,".

In column 2, line 23, replace "pulse" with "pulses".

Signed and Sealed this

Twenty-sixth Day of May, 1998

Attest:

BRUCE LEHMAN

*Attesting Officer*   *Commissioner of Patents and Trademarks*